United States Patent [19]

Madaus et al.

[11] Patent Number: 4,830,970
[45] Date of Patent: * May 16, 1989

[54] NUTRIENT SUBSTRATE CARRIER

[75] Inventors: Rolf Madaus, Am Wildwechsel; Gerhard Bruesewitz, Uhlweg, both of Fed. Rep. of Germany

[73] Assignee: Dr. Madaus & Co., Cologne, Fed. Rep. of Germany

[*] Notice: The portion of the term of this patent subsequent to Sep. 1, 2004 has been disclaimed.

[21] Appl. No.: 848,072

[22] Filed: Apr. 4, 1986

Related U.S. Application Data

[63] Continuation of Ser. No. 724,807, Apr. 19, 1985, abandoned, which is a continuation of Ser. No. 375,638, May 6, 1982, abandoned.

[30] Foreign Application Priority Data

May 16, 1981 [DE] Fed. Rep. of Germany ....... 3119541

[51] Int. Cl.⁴ .................. C12M 1/24; C12M 1/16; C12M 1/18
[52] U.S. Cl. .................................. 435/296; 435/299; 435/300
[58] Field of Search .................. 435/30, 287, 292, 293, 435/294, 296, 299, 300, 301, 800, 810; 426/34

[56] References Cited

U.S. PATENT DOCUMENTS

| 2,874,091 | 2/1959 | Fisk | 435/810 |
| 3,308,039 | 3/1967 | Nelson | 435/293 |
| 3,474,004 | 10/1969 | Fink | 435/810 |
| 3,651,926 | 3/1972 | Elfast, Jr. | 435/296 |
| 3,849,256 | 11/1974 | Linder | 435/300 |
| 4,022,914 | 5/1977 | Moody | 426/34 |
| 4,271,270 | 6/1981 | Lukaczek | 435/294 |
| 4,690,896 | 9/1987 | Brusewitz et al. | 435/300 X |

Primary Examiner—Robert J. Warden
Assistant Examiner—Randall E. Deck
Attorney, Agent, or Firm—Felfe & Lynch

[57] ABSTRACT

The present invention provides a prepared nutrient substrate carrier for the qualitative and quantitative determination of micro-organisms, comprising an object carrier coated with at least one nutrient substrate, which object carrier is firmly attached to a lid and, during storage and during incubation, is present in a transparent vessel which can be securely closed with a lid, wherein the coated object carrier is enclosed in an envelope during storage, said envelope being adapted to be easily removed before inoculation.

6 Claims, 2 Drawing Sheets

NUTRIENT SUBSTRATE CARRIER

This application is a continuation of Ser. No. 724,807, filed Apr. 19, 1985, abandoned, which is a continuation of Ser. No. 375,638, filed May 6, 1982, abandoned.

This invention relates to a pre-prepared nutrient substrate carrier for the qualitative and quantitative determination of microorganisms, especially of pathogens.

Prepared nutrient substrate carriers are known and generally comprise an object carrier coated with at least one nutrient substrate which is firmly connected with a screw-threaded lid and, during storage during incubation, is present in a transparent screw-threaded vessel securely screwed on to the screwthreaded lid. These prepared nutrient substrate carriers are used for diagnostic purposes and for testing for the content of microorganisms in industrial processes, as well as for hygienic control, for which purposes the substrate carrier is either dipped into the material to be tested or this material is dabbed on to the substrate carrier.

The most frequently used prepared nutrient substrate carriers usually consist of a rectangular synthetic resin carrier as the object carrier, most of which are coated on both sides with at least one nutrient substrate.

An important disadvantage of the known prepared nutrient substrate carriers is their poor storage stability. Since the nutrient substrate contains a large amount of water, even in the case of laborious and most careful storage, it is scarcely possible to avoid the evaporation of some of the water which then deposits on the vessel walls or on the lid. Dried out nutrient substrates are completely useless. When the collected condensed water, due to occasional movement or during transport, flows back or is splashed back on to the nutrient substrate surface, inhomogeneities on the surface of the substrate result. Especially when different nutrient substrates are present side by side, this can give rise to undesirable displacements of specific soluble components of the nutrient substrate, resulting in a loss of specificity of the substrates which thus, in practice, become useless.

The preparation of the hitherto known prepared nutrient substrate carriers is very laborious from a technical and economic point of view. Especially in the case of object carriers with different nutrient substrates, these must be applied side by side and individually cooled. These working steps must be carried out under absolutely micro-organism-free conditions, right up to the final packing of the whole of the prepared nutrient substrate carrier.

It is an object of the present invention to overcome the errors and losses due to the evaporation and condensation of the water present in the nutrient substrate. A further object of the present invention is to improve the production of the microscope carriers in a technically and thus economically improved manner.

Thus, according to the present invention, there is provided a prepared nutrient substrate carrier for the qualitative and quantitative determination of microorganisms, comprising an object carrier coated with at least one nutrient substrate, which object carrier is firmly attached to a lid and, during storage and during incubation, is present in a transparent vessel which can be securely closed with a lid, wherein the coated object carrier is enclosed in an envelope during storage, said envelope being adapted to be easily removed before inoculation.

The space between the envelope and the vessel acts as a heat insulator and prevents, to a considerable extent, the formation of water of condensation on the inner wall of the envelope. Thus, the prepared nutrient substrate carriers according to the present invention neither tend to dry out nor to become spoiled due to flowing and splashing of water of condensation.

In the simplest case, the envelope can consist of a synthetic resin foil which is impermeable to water vapour, the upper end of which is stuck or welded on to a screw lid and the other end of which is closed, for example by adhesion or welding. In a preferred embodiment of the present invention, the envelope is in the form of a rigid collar which leaves free no or only a relatively small space between itself and the coated object carrier. Such collars are, after coating the object carrier, placed in an inverted position over the object carrier and tightly pressed against the lid.

Especially in the case of rigid or relatively shape-stable envelopes, it is, in principle, also possible to invert these over the object carrier before coating the object carrier with the nutrient substrate and then completely to fill the hollow, fillable intermediate space with the nutrient substrate. In this case, the volume between the collar and the object carrier is zero. In the case of this embodiment, it is necessary to ensure that the nutrient substrate only has a poor adhesion to the envelope but is very firmly attached to the object carrier so that the envelope can be removed without damaging the nutrient substrate. By appropriate choice of the materials, it is possible to achieve a differing adhesion of the envelope and of the object carrier to the nutrient substrate. In addition, attachment on to the object carrier can be strengthened by ribs or knubs. In the case of this embodiment, the lid is only connected to the object carrier after introduction of the nutrient substrate(s). This can admittedly be carried out by adhesion but the lid is preferably attached to the microscope slide by a snap closure (FIG.12).

The nutrient substrate carrier according to the present invention will now be described in more detail, with reference to the accompanying drawings, which illustrate several specific embodiments.

FIG. 1 is a longitudinal section through a nutrient substrate carrier according to the present invention, FIGS. 2 to 11 are cross-sections through coated microscope slides and envelopes in appropriate vessels and FIG. 12 illustrates a microscope slide which is connected to the lid by means of a snap closure.

In these Figures, 1 is a transparent vessel on to which a lid 2 can be securely screwed, 3 is an object carrier, 4 is a nutrient substrate, 5 is an envelope, 6 is an elastic seal and 7 is a convexity on the base of the envelope which ensures that the envelope can be firmly pressed against the seal 6 when the lid 2 is screwed down.

The object carrier can, of course, also have three, five or more arms. The envelope can then also be round or preferably triangular, pentagonal or polygonal (see FIGS. 6 to 11).

Instead of the hitherto usually employed vessels with screw lids, according to the present invention it is also possible to use a vessel upon which a lid is pressed with a snap closure.

According to the present invention, it is, in principle, possible to use all known nutrient substrates, for example the CLED nutrient substrates for the determination of the total content of microorganisms in urine. In the case of object carriers with two different nutrient substrates, to one side there can again preferably be applied a CLED agar and on the other side a MacConkey agar which selectively only makes gram-negative bacteria visible. In the case of an object carrier with four different nutrient substrates, there can be combined, for example, a CLED agar, a MacConkey agar, a cetrimide agar and a Nickerson medium. The cetrimide agar enables the Pseudomonas group of micro-organisms to be detected, whereas the Nickerson medium serves for the detection of fungi and yeasts.

A nutrient substrate can, of course, be further divided up into an upper and lower part so that twice as many different nutrient substrates can be applied to one object carrier.

Figure 1:
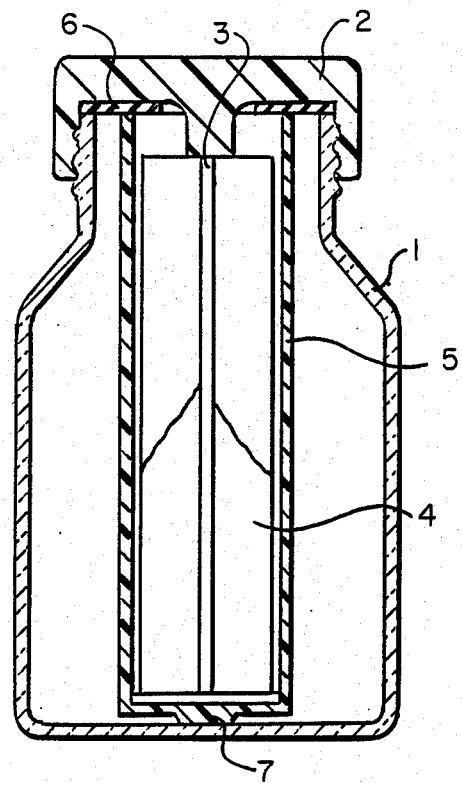
Figure 2:
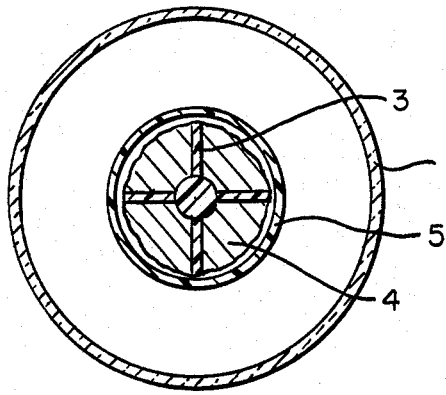
FIG. 2 illustrates an object carrier into which up to four different nutrient substrates can be introduced. In this case, the envelope 5 is rigid and round in cross-section and can, as in the case of FIG. 1, be pressed against the seal 6 by means of a convexity on the base thereof.
Figure 3:
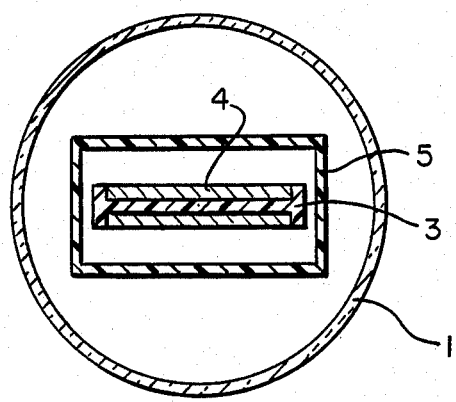
FIG. 3 shows another conventional arrangement of the object carrier to which two different nutrient substrates can be applied. In this case, the envelope is rectangular and rigid and can again also be pressed against the seal in the screwed lid by means of a convexity on the base thereof.
Figure 4:
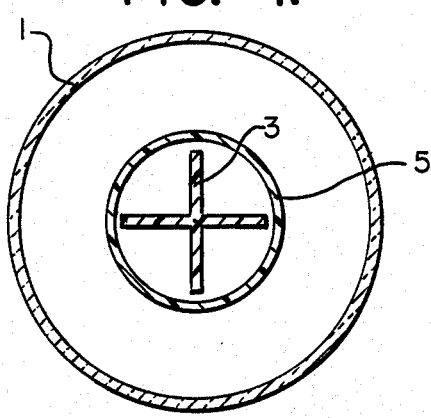
FIGS. 4 and 5 show object carriers upon which it is again possible to apply up to four different nutrient substrates. In these cases, the envelope applied has a round or quadratic cross-section and can also be used as a moulded shape.
Figure 5:
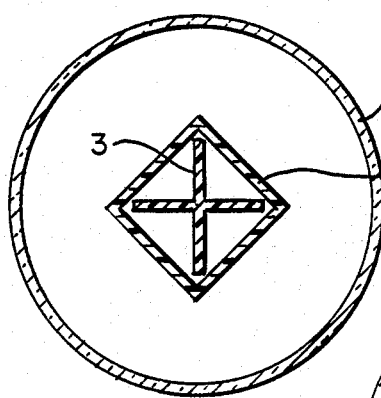
Figure 6:
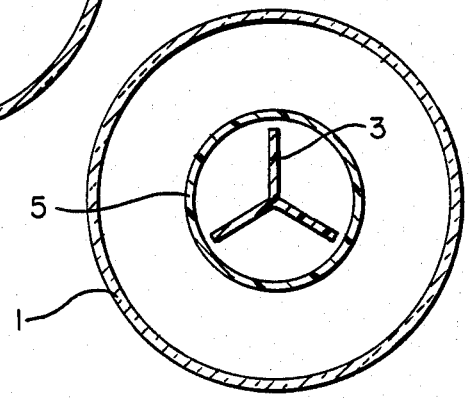
Figure 7:
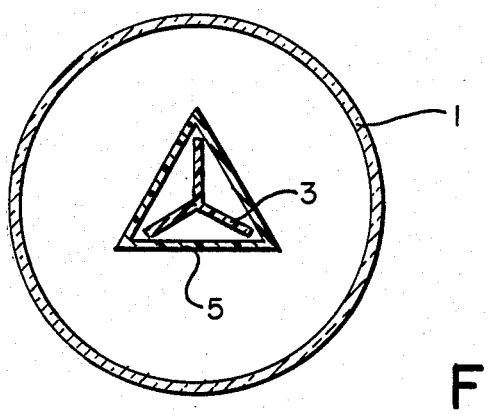
Figure 8:
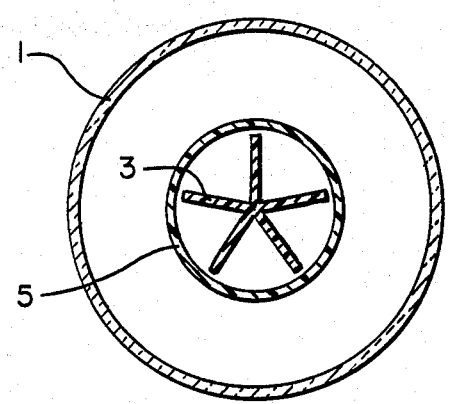
Figure 9:
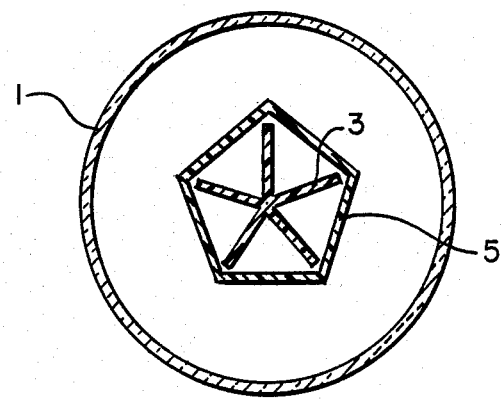
Figure 10:
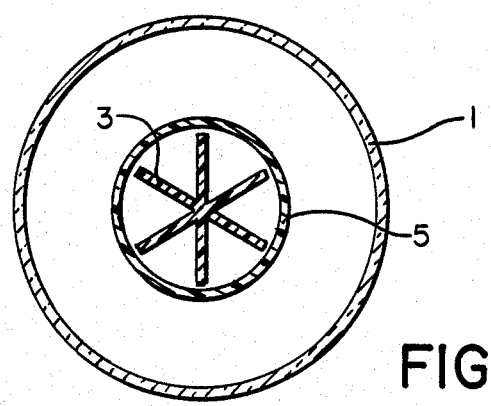
Figure 11:
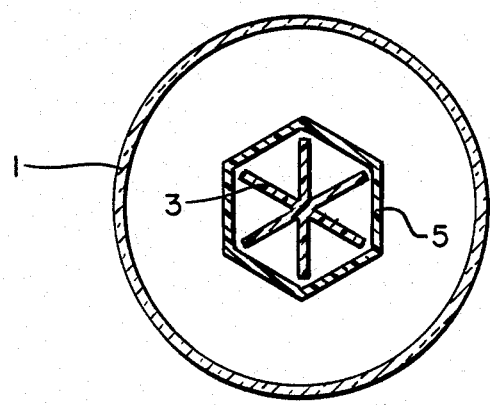
Figure 12:
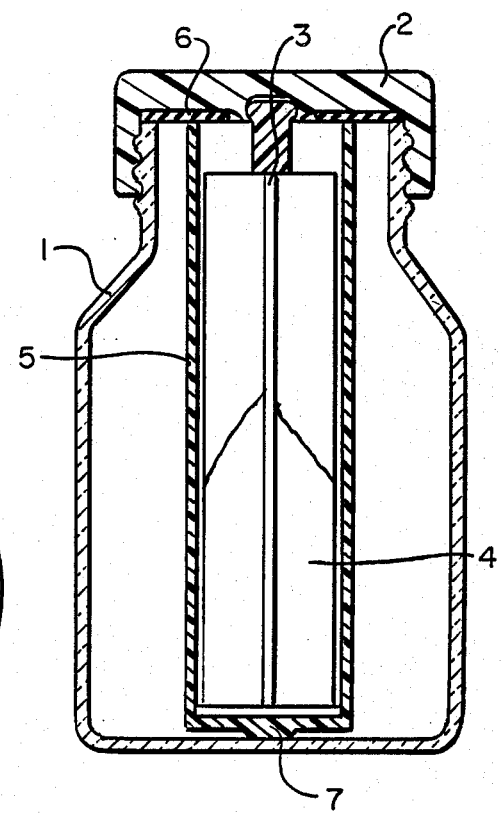

In order to use the nutrient substrate carrier according to the present invention, the transparent screw-topped vessel is opened and the envelope 5 removed and discarded. Thereafter, either the whole of the object carrier is dipped into a liquid sample to be investigated, for example urine, and, after dipping off, is again placed into the screw-topped vessel and incubated. Instead of dipping into a urine sample or other liquid sample, it is, of course, also possible to apply a part thereof or cultures to appropriate areas, for example with a pipette or wire loop. Especially in the case of nutrient substrates which project beyond the object carrier, for example as in FIG. 3, inoculation can also be carried out by dabbing or rolling on the sample to be investigated. After incubation, evaluation takes place in the usual manner.

For simplification of the evaluation, it is, of course, also possible partly or wholly to colour the object carrier in order to achieve a better color contrast.

It will be understood that the specification and examples are illustrative but not limitative of the present invention and that other embodiments within the spirit and scope of the invention will suggest themselves to those skilled in the art.

What is claimed is:

1. A nutrient substrate carrier comprising:
   (a) an object carrier for being coated with at least one nutrient substrate having an intermediate hollow space and a lid connecting means;
   (b) a removable transparent, form-stable envelope applied to said object carrier so as to cover and form a fillable space with said intermediate hollow space;
   (c) a transparent vessel having a means for screwing a lid thereto; and
   (d) a lid which engages said transparent vessel and connects to said object carrier.

2. Nutrient substrate carrier as claimed in claim 1, wherein the envelope has a round or polygonal cross-section.

3. Nutrient substrate carrier as claimed in claim 1, wherein the object carrier has a rectangular cross-section.

4. Nutrient substrate carrier as claimed in claim 1, wherein the object carrier has a multi-segmented or cruciform cross-section.

5. Nutrient substrate of claim 1, wherein said envelope is a rigid collar which leaves substantially no free space between said collar and said object carrier when said object carrier is coated with a nutrient substrate.

6. Nutrient substrate carrier of claim 1, wherein said object carrier is coated with at least one nutrient substrate.

* * * * *